US011548837B2

(12) United States Patent
Brown et al.

(10) Patent No.: US 11,548,837 B2
(45) Date of Patent: Jan. 10, 2023

(54) SELF CLEANING REACTOR SYSTEM

(71) Applicant: NOVA Chemicals (International) S.A., Fribourg (CH)

(72) Inventors: Stephen Brown, Calgary (CA); Peter Zoricak, Calgary (CA); Eric Clavelle, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 938 days.

(21) Appl. No.: 16/386,974

(22) Filed: Apr. 17, 2019

(65) Prior Publication Data

US 2019/0241483 A1 Aug. 8, 2019

Related U.S. Application Data

(62) Division of application No. 15/126,792, filed as application No. PCT/IB2015/050785 on Feb. 2, 2015, now abandoned.

(30) Foreign Application Priority Data

Mar. 27, 2014 (CA) ................................ CA 2847814

(51) Int. Cl.
| | | |
|---|---|---|
| *C07C 2/32* | (2006.01) | |
| *B01J 8/10* | (2006.01) | |
| *B01J 19/18* | (2006.01) | |
| *C07C 2/36* | (2006.01) | |
| *B01J 14/00* | (2006.01) | |
| *B01J 19/00* | (2006.01) | |

(52) U.S. Cl.
CPC ................ *C07C 2/32* (2013.01); *B01J 8/10* (2013.01); *B01J 14/00* (2013.01); *B01J 19/002* (2013.01); *B01J 19/0066* (2013.01); *B01J 19/18* (2013.01); *C07C 2/36* (2013.01); *B01J 2208/00867* (2013.01); *B01J 2219/00033* (2013.01); *B01J 2219/0099* (2013.01); *B01J 2219/00247* (2013.01); *B01J 2219/00252* (2013.01); *C07C 2531/14* (2013.01); *C07C 2531/22* (2013.01); *C07C 2531/24* (2013.01); *C07C 2531/34* (2013.01)

(58) Field of Classification Search
CPC ......... C07C 2/32; C07C 2/36; C07C 2531/14; C07C 2531/22; C07C 2531/24; C07C 2531/34; B01J 8/10; B01J 14/00; B01J 19/002; B01J 19/0066; B01J 19/18; B01J 2208/00867; B01J 2219/00033; B01J 2219/000247; B01J 2219/00252; B01J 2219/0099
See application file for complete search history.

(56) References Cited

U.S. PATENT DOCUMENTS

| | | | | |
|---|---|---|---|---|
| 4,300,625 A | * | 11/1981 | Mikhailov | ............. B01J 19/002 165/95 |
| 8,227,653 B2 | * | 7/2012 | Weber | .................... C08F 2/005 526/75 |
| 8,252,956 B2 | | 8/2012 | Gao et al. | |
| 9,421,533 B2 | * | 8/2016 | Wang | .................. B01J 31/1616 |
| 2004/0194805 A1 | * | 10/2004 | Reisinger | .................. B08B 9/08 134/7 |

FOREIGN PATENT DOCUMENTS

CA 2 708 011 A1 12/2011

OTHER PUBLICATIONS

Paul, Edward L., Atiemo-Obeng, Victor A. and Kresta, Suzanne M.; Handbook of Industrial Mixing—Science and Practice; 10 Solid Liquid Mixing; 10-3 Measurements and Correlations for Solid Suspension and Distribution; Copyright 2004 by John Wiley & Sons, Inc., pp. 557-564.

* cited by examiner

*Primary Examiner* — Ali Z Fadhel
(74) *Attorney, Agent, or Firm* — Thomas J. Styslinger

(57) ABSTRACT

This invention relates to a self cleaning reactor and to a process for the oligomerization of ethylene that employs a self-cleaning reactor. The reactor includes a mass of inert, particulate cleaning bodies that are entrained by the liquid in the reactor and scour the internal surfaces of the reactor during normal operation. This scouring action reduces the level of fouling on the reactor surfaces. Foulant material (polyethylene) is removed from the process on a continuous basis but the cleaning bodies remain within the reactor.

10 Claims, No Drawings

SELF CLEANING REACTOR SYSTEM

REFERENCE TO RELATED APPLICATION

This application is a divisional of U.S. Ser. No. 15/126,792, filed Sep. 16, 2016, entitled Self Cleaning Reactor System" which is herein incorporated by reference in its entirety.

TECHNICAL FIELD

This invention relates to the oligomerization of ethylene using a self cleaning reactor.

BACKGROUND ART

Many chemical reactions cause reactor fouling. The reactor of this invention is intended for use in a process that produces a desired liquid hydrocarbon product (ethylene oligomers) and an undesired polymeric by-product (polyethylene).

The by-product polymer causes fouling of internal reactor surfaces such as reactor walls, baffle surfaces and impeller shafts and blades. Over the course of time, the fouling becomes severe enough that the reactor must be shut down and cleaned. Examples of commonly used cleaning methods include chemical cleaning (using a hot solvent, detergent or a combination of the two); mechanical cleaning (using high pressure water or solvent; brushes, and/or cutting techniques) and combination of chemical and mechanical cleaning techniques.

This invention mitigates reactor fouling problems with a self-cleaning function that performs during the normal operation of the reactor. The reactor uses a large number of inert, particulate cleaning bodies. These cleaning bodies are entrained by the reactor liquid and are directed against the internal reactor surfaces. The motive force for the reactor liquid is also useful for mixing the liquid reactor contents. Contact between the cleaning bodies and the reactor surfaces provides an abrasive action that cleans the reactor surfaces, and/or prevents the polyethylene from sticking to the surfaces.

A prior art system that provides in-situ cleaning of heat exchangers is sold by the Taprogge company of Wetter, Germany. The Taprogge heat exchanger cleaning system uses a plurality of polymeric spheres that are forced through the tube side of a water cooled, shell and tube exchanger. The cleaning balls scour the inside of the tubes and thereby remove foulants (such as sediment) from the cooling water that flows through the tubes. However, it will be appreciated that the size of the cleaning spheres must be closely matched to the internal tube diameter. Abrasion of cleaning spheres (or loss of elasticity, in the case of rubber spheres) can limit the service life of the cleaning balls and frequent replacement of the cleaning spheres can be necessary. For example, it has been reported that cleaning spheres made from natural rubber typically require replacement after four weeks.

The present invention uses a much larger number of smaller cleaning bodies. These cleaning bodies do not need to be "size matched" to any particular surface dimension (whereas the diameter of the Taprogge cleaning bodies is size matched to the exchanger tube diameter). In general, the cleaning bodies of this invention are simpler, more robust and easier to maintain than the cleaning spheres of the Taprogge technology.

DISCLOSURE OF INVENTION

In one embodiment, this invention provides a self cleaning, continuous flow reactor, said reactor comprising:

1) at least one inlet line for liquid reactants;
2) at least one outlet line for liquid products;
3) a mixing system to mix liquid contained within said reactor;
4) a mass of cleaning bodies contained within said reactor, with the provisos that
   a) said mixing system provides sufficient liquid velocity to suspend said cleaning bodies within said reactor;
   b) said cleaning bodies have a particle size of from 2 millimeters to 2 centimeters; and
   c) said cleaning bodies are retained within said reactor during operation of the reactor.

In another embodiment, the present invention provides: a process for the removal of by-product polyethylene from a continuous flow, mixed, oligomerization reactor, said process comprising:

a) providing input flows comprising ethylene, solvent, and an oligomerization catalyst system to said reactor;
b) oligomerizing ethylene under continuous flow conditions within said reactor; and
c) providing a discharge stream from said reactor comprising solvent, oligomer product and polyethylene by-product; characterized in that said process is conducted in the presence of a mass of reactor cleaning bodies, with the proviso that substantially all of said cleaning bodies remain within said reactor during said process.

BEST MODE FOR CARRYING OUT THE INVENTION

Cleaning Bodies

The cleaning bodies can be of any shape and of any material that can be suspended and circulated by the agitation system used in the reactor. Cleaning body material selection will also be dictated by compatibility with the process and the reactor system components such as agitators, draft tube, shaft(s), baffles, injectors and the vessel wall.

The cleaning bodies are preferably made from a material that is less hard than the hardness of the materials used to construct the reactor system components to avoid undue abrasion/erosion of the reactor system components. The term "hardness" is meant to convey its conventional meaning in the context of the well-known Mohs hardness scale. For example, silica is known to be hard (and it has a high Mohs hardness number) and the use of silica could lead to the abrasion of the reactor system components.

The cleaning bodies should also be "inert"—which, in the context of this invention, is intended to mean that the cleaning bodies do not adversely affect the catalyst system that is used in the oligomerization reactor.

The cleaning bodies should also be "suspended" in the reaction medium—i.e. the particles should not remain on the bottom of the reactor during the process of this invention. Persons skilled in the art will recognize that several factors will affect the ability of a solid particle to become suspended in a mixed liquid, including the particle size and density; the type and speed of agitation and the fluid viscosity. One correlation that may be used to estimate the "just suspended speed" for an agitated reactor was developed by Zweitering:

$$Njs = S\left(\frac{\mu}{\rho}\right)^{0.1} \left[\frac{g(\rho_p - \rho)}{\rho}\right]^{-0.45} X^{0.13} d_p^{0.2} D^{-0.85} \quad \text{"- Correlation 1-"}$$

where the terms of the correlation are defined as follows (with units in parenthesis):
Njs is the just suspended speed (rad/second),
S a coefficient specific to a particular agitation system (dimensionless),
μ the liquid viscosity (Pascals/seconds),
ρ the liquid density (kilogram/meter$^3$),
g the gravitational constant (9.81 meters/second$^2$),
ρp the cleaning body density (kilogram/meter$^3$),
X the mass ratio of suspended solids to liquid×1000 (dimensionless),
dp the cleaning body characteristic diameter (meters), and
D the agitator characteristic diameter (meters).

The agitator speed N must typically be larger than Njs speed to ensure that the cleaning bodies do not settle on the floor of the reactor vessel or other horizontal surface. In general, the agitator needs to operate at a multiple of this speed to ensure good circulation and thus good, sufficient cleaning action throughout the vessel. The multiple will depend on the agitation system. For example, a draft tube and agitator system will require a lower multiple than a system with an agitator and no draft tube or an agitator and no baffles for example.

The cleaning bodies do not need to be of equal diameter. A distribution of diameters can be advantageous in increasing the cleaning effectiveness. In addition, binary mixtures can be used to lower the liquid velocity that is required to suspend the cleaning bodies ("Njs" in the correlation, below).

The agitation system can be an agitator or agitators in a baffled or unbaffled tank. For vessels with internal height to internal diameter ratios over 1.25, it may be necessary to have multiple agitators to ensure circulation throughout the vessel. The use of a draft tube is another option; and the combination of multiple agitators with a draft tube may be optimum. The agitation system is not limited to a system with rotating impellers—for example, a series of jets may provide the required mixing.

The correlation described above may be used for reactions equipped with an agitator.

The following correlation is more suitable for a reactor that is equipped with mixing jets:

$$Vjs = 2\left(\frac{(\rho_p - \rho)}{\rho}\right)^{2.08} \frac{\left(\frac{\mu}{\rho}\right)^{0.16} g^{0.42} T^{1.16} d_p^{0.1} C_w^{0.24}}{D_J}$$

where the terms of the equation are defined as follows (with units in parenthesis):
Vjs is the just suspended jet speed,
μ is the liquid viscosity (Pascals/seconds),
ρ is the liquid density (kilogram/meter$^3$),
G is the gravitational constant (9.81 meters/second$^2$),
ρp is the cleaning body density (kilogram/meter$^3$),
T is the tank diameter,
dp is the cleaning body characteristic diameter (meters),
Cw is the percent weight fraction of solids (based on the weight of the solids/weight of solids+reaction medium), and
Dj is the jet diameter.

The coefficient s has a value of typically between 3.0 and 8.0 depending on the reactor geometry and agitator type and number of agitators for (continuously stirred reactors).

The correlations described above are discussed in further detail in Handbook of Industrial Mixing—Science and Practice, Edited by Edward L. Paul, Victor A. Atiemo-Obeng, Suzanne M. Kresta, Wiley-Interscience, 2004, at pages 558-564.

These correlations provide a useful starting point for estimating the agitator speed that is required to suspend a given mass of cleaning bodies having a known particle size and density. In the alternative, for a given (known) agitator speed in a known reactor volume, the maximum particle size and/or density of a potential cleaning body can be estimated.

The particle size of the cleaning bodies is preferably from about 2 millimeters to about 2 centimeters. While not wishing to be bound by theory, it is believed that the cleaning bodies remove foulant (polyethylene) from the reactor walls by a physical scrubbing/scouring action. Accordingly, it is believed that momentum transfer (from the cleaning body to the foulant) is required for successful cleaning and it is for this reason that a minimum particle size of 2 mm is preferred. Particle sizes of greater than 2 cm may be useful, but it becomes more difficult to "suspend" a cleaning body of a greater density as the particle size increases.

The density of the cleaning bodies is preferably greater than the density of the oligomerization medium (so that the cleaning bodies do not float).

The upper limit on the density of the cleaning bodies is limited by the ability of the agitator system to suspend the cleaning bodies. The use of higher densities can make it difficult to suspend the cleaning bodies at reasonable agitator speeds in the small reactors. However, as will be clear to persons of skill in the art, this problem diminishes with larger reactors—i.e. the fluid velocity that is provided by the larger agitators in larger reactors is sufficient to suspend cleaning bodies having a higher density. Thus, although the accompanying examples illustrate the use of cleaning bodies having a relatively low density (in a small reactor), the correlations given above indicate that cleaning bodies having a higher density/specific gravity are suitable for use in larger reactors. The use of cleaning bodies having a higher density can be desirable (provided that they are suspended) because they can provide more momentum/cleaning action as they come in contact with the foulant on the internal surfaces of the reactor.

The upper limit on the density of the cleaning bodies may be calculated/estimated from correlation 1 above—and is a function of the particle size of the cleaning bodies; the mass of cleaning bodies; the rate of agitation (fluid velocity) and fluid viscosity. As a practical matter, it is preferred to use a cleaning body having a density of less than 7 grams per cubic centimeter (especially less than 3 g/cc) given the power requirements that would be necessary to suspend denser cleaning bodies.

It is important to note that the cleaning bodies remain within the reactor, but the foulant (polyethylene) is removed from the reactor during the process of this invention.

This allows long reaction "runtimes" without severe reactor fouling. The foulant is removed from the reactor with the product stream and may be observed in the product stream as small particles or flakes.

Catalyst System for Oligomerization Process

The catalyst system used in the process of the present invention must contain three essential components, namely:
(i) a source of chromium;
(ii) a diphosphine ligand; and
(iii) an activator.

Preferred forms of each of these components are discussed below.

Chromium Source

Any source of chromium that is soluble in the process solvent and which allows the oligomerization process of the present invention to proceed may be used. Preferred chromium sources include chromium trichloride; chromium (III) 2-ethylhexanoate; chromium (III) acetylacetonate and chromium carbonyl complexes such as chromium hexacarbonyl. It is preferred to use very high purity chromium compounds as these should generally be expected to minimize undesirable side reactions. For example, chromium acetylacetonate having a purity of higher than 99% is commercially available (or may be readily produced from 97% purity material—using recrystallization techniques that are well known to those skilled in the art). The present process preferably operates at a temperature of from 30 to 50° C. We have observed that very low Cr concentrations in the reactor are optimum for this temperature—with a range of 0.1 to $3\times10^{-6}$ molar being suitable and from 0.3 to $0.8\times10^{-6}$ being optimum.

Diphosphine Ligand Used in the Oligomerization Process

In general, the ligand used in the process of this invention is defined by the formula $(R^1)(R^2)$—$P^1$-bridge-$P^2(R^3)(R^4)$ wherein $R^1$, $R^2$, $R^3$ and $R^4$ are independently selected from the group consisting of hydrocarbyl and heterohydrocarbyl and said bridge is a moiety that is bonded to both phosphorus atoms.

The term hydrocarbyl as used herein is intended to convey its conventional meaning—i.e. a moiety that contains only carbon and hydrogen atoms. The hydrocarbyl moiety may be a straight chain; it may be branched (and it will be recognized by those skilled in the art that branched groups are sometimes referred to as "substituted"); it may be saturated or contain unsaturation and it may be cyclic. Preferred hydrocarbyl groups contain from 1 to 20 carbon atoms. Aromatic groups—especially phenyl groups—are especially preferred. The phenyl may be unsubstituted (i.e. a simple $C_6H_5$ moiety) or contain substituents, particularly at an ortho (or "o") position.

Similarly, the term heterohydrocarbyl as used herein is intended to convey its conventional meaning—more particularly, a moiety that contains carbon, hydrogen and at least one heteroatom (such as O, N, R and S). The heterohydrocarbyl groups may be straight chain, branched or cyclic structures. They may be saturated or contain unsaturation. Preferred heterohydrocarbyl groups contain a total of from 2 to 20 carbon+heteroatoms (for clarity, a hypothetical group that contains 2 carbon atoms and one nitrogen atom has a total of 3 carbon+heteroatoms).

It is preferred that each of $R^1$, $R^2$, $R^3$ and $R^4$ is a phenyl group (with an optional substituent in an ortho position on one or more of the phenyl groups).

Highly preferred ligands are those in which $R^1$ to $R^4$ are independently selected from the group consisting of phenyl and o-fluorophenyl. The resulting ligands are useful for the selective tetramerization of ethylene to octene-1 with some co product hexene also being produced.

The term "bridge" as used herein with respect to the ligand refers to a moiety that is bonded to both of the phosphorus atoms in the ligand—in other words, the "bridge" forms a link between $P^1$ and $P^2$. Suitable groups for the bridge include hydrocarbyl and an inorganic moiety selected from the group consisting of $N(CH_3)$—$N(CH_3)$—, —$B(R^6)$—, —$Si(R^6)_2$—, —$P(R^6)$— or —$N(R^6)$— where $R^6$ is selected from the group consisting of hydrogen, hydrocarbyl and halogen.

It is especially preferred that the bridge is —$N(R^5)$— wherein $R^5$ is selected from the group consisting of hydrogen, alkyl, substituted alkyl, aryl, substituted aryl, aryloxy, substituted aryloxy, halogen, alkoxycarbonyl, carbonyloxy, alkoxy, aminocarbonyl, carbonylamino, dialkylamino, silyl groups or derivatives thereof and an aryl group substituted with any of these substituents. Highly preferred bridges are those in which $R^5$ is a $C_1$ to $C_{12}$ alkyl—especially isopropyl (i.e. when $R^5$ is isopropyl).

Activator (or "Co-Catalyst")

The activator may be any compound that generates an active catalyst for ethylene oligomerization. Mixtures of activators may also be used. Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminium compounds include compounds of the formula AlRS, where each R is independently $C_1$-$C_{12}$ alkyl, oxygen or halide, and compounds such as $LiAlH_4$ and the like. Examples include trimethylaluminium (TMA), triethylaluminium (TEAL), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes (also referred to as aluminoxanes). Alumoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available alumoxanes are generally believed to be mixtures of linear and cyclic compounds. The cyclic alumoxanes can be represented by the formula $[R^8AlO]_S$ and the linear alumoxanes by the formula $R^7(R^8AlO)_S$ wherein s is a number from about 2 to 50, and wherein $R^6$, $R^7$, and $R^8$ represent hydrocarbyl groups, preferably $C_1$ to $C_6$ alkyl groups, for example methyl, ethyl or butyl groups. Alkylalumoxanes especially methylalumoxane (MAO) are preferred.

It will be recognized by those skilled in the art that commercially available alkylalumoxanes may contain a proportion of trialkylaluminium. For instance, some commercial MAO contains up to 35 weight % trimethylaluminium (TMA), and commercial "modified MAO" (or "MMAO") contains both TMA and TIBA. Quantities of alkylalumoxane are generally quoted herein on a molar basis of aluminium (and include such "free" trialkylaluminium).

A combination of a MAO with additional TEAL is preferred for this invention. The combined use of MAO and TEAL can provide a cost effective cocatalyst system.

In the preparation of the catalyst systems used in the present invention, the quantity of activating compound to be employed is easily determined by simple testing, for example, by the preparation of small test samples which can be used to oligimerize small quantities of ethylene and thus to determine the activity of the produced catalyst. It is generally found that the quantity employed is sufficient to provide 500 to 5,000 moles of aluminium per mole of chromium. A mix of MAO and TEAL is preferred with the moles of aluminum from the MAO that are provided being about 40 to 60 mole % of the total moles of aluminum in the activator. Molar Al/Cr ratios of from 1000/1 to 3500/1 are preferred. Additional TEAL increases the total Al/Cr ratio but may actually reduce overall costs as TEAL is much less expensive than MAO. The use of a combined MAO+TEAL cocatalyst system is shown in the examples. We have also found that the overall concentration of aluminum in the reactor should be from 1000 to 3000×10$^{-6}$ molar.

Part B Hydrogen

The use of hydrogen is highly preferred in the process of the present invention. Optimum ethylene:hydrogen ratios (weight:weight in the feed) are believed to be from 150/1 to 800/1.

Part C Catalyst: Ratios and Preparation

For oligomerizations at temperatures higher than 50° C., the chromium and ligand may be present in almost any molar ratio in which the ligand is provided in a molar excess to the chromium. Stated alternatively: a molar equivalent of ligand and chromium provides an active catalyst and excess ligand (though not necessary) does not generally have an adverse impact upon activity at high temperature. At lower temperatures, we have observed a negative impact upon catalyst activity when a molar excess of ligand (to Cr) is used. The optimum ligand:Cr ratio has been observed to be from 0.7/1 to 1.0/1, especially from 0.75/1 to 0.85/1, at temperatures of from 30 to 50° C.

A variety of methods are known to purify solvents used to prepare the catalysts including use of molecular sieves (3A), adsorbent alumina and supported de-oxo copper catalyst. Several configurations for the purifier system are known and depend on the nature of the impurities to be removed, the purification efficiency required and the compatibility of the purifier material and the process solvent. In some configurations, the process solvent is first contacted with molecular sieves, followed by adsorbent alumina, then followed by supported de-oxo copper catalyst and finally followed by molecular sieves. In other configurations, the process solvent is first contacted with molecular sieves, followed by adsorbent alumina and finally followed by molecular sieves. In yet another configuration, the process solvent is contacted with adsorbent alumina. One preferred purifier system consists of molecular sieves, followed by adsorbent alumina and finally followed by another set of molecular sieves.

Part D Reaction Conditions (General)

Irrespective of the process conditions employed, the oligomerization is typically carried out under conditions that substantially exclude oxygen, water, and other materials that act as catalyst poisons. In addition, the reactor is preferably purged with a nonreactive gas (such as nitrogen or argon) prior to the introduction of catalyst. A purge with a solution of MAO and/or aluminum alkyl may also be employed to lower the initial level of catalyst poisons. Also, oligomerizations can be carried out in the presence of additives to control selectivity, enhance activity and reduce the amount of polymer formed in oligomerization processes.

The process of this invention requires the use of a solvent or diluent because the undesirable formation of $C_{10}^+$ oligomers has been observed to increase under continuous flow oligomerization conditions when the concentration of octene in the reactor increases. The addition of a solvent mitigates this problem. Suitable solvents include saturated $C_6$ to $C_{20}$ aliphatics (such as hexane, heptane, etc.) and saturated cycloaliphatics (such as cyclohexane or methyl cyclohexane). Unsaturated aliphatics (especially 1-olefins such as 1-hexene; 1-heptene and 1-octene) should be avoided because the use of such unsaturates has been observed to lead to the undesired formation of higher oligomers.

Mixtures of inert diluents or solvents also could be employed. The preferred solvents are aromatic hydrocarbons or saturated aliphatics such as, for example, isobutane, pentane, toluene, xylene, ethylbenzene, cumene, mesitylene, heptane, cyclohexane, methylcyclohexane, chlorobenzene, dichlorobenzene, and mixtures of aliphatics sold under the trademark Isopar®. Cyclohexane and linear $C_6$ to $C_{10}$ saturated aliphatics are especially preferred. Heptane is an especially preferred linear aliphatic because it is readily separated from the oligomers produced by this reaction using conventional distillation techniques.

The ethylene feedstock for the oligomerization may be substantially pure or may contain other olefinic impurities and/or ethane.

The feedstock is preferably treated to remove catalyst poisons (such as oxygen, water and polar species) using techniques that are well known to those skilled in the art. The technology used to treat feedstocks for polymerizations is suitable for use in the present invention and includes the molecular sieves, alumina and de-oxo catalysts described above for analogous treatment of the process solvent.

Reactor

The present invention must be conducted under continuous flow conditions using a mixed reactor.

The term "continuous flow" is meant to convey its conventional meaning—i.e. reactants are continuously added to the reactor and product is continuously withdrawn.

Similarly, the term "mixed reactor" is meant to convey its conventional meaning—i.e. a reactor that contains an agitator or mixing system. A continuously stirred tank reactor ("CSTR") is generally preferred. However, a loop reactor in which mixing is provided by a circulating pump is also suitable (and such reactors are well known to those skilled in the art and are in commercial use).

The use of a CSTR is generally preferred as it is desirable to maintain essentially homogenous reactor conditions—i.e. as will be appreciated by those skilled in the art, a well mixed CSTR will provide homogenous reactor conditions (in contrast to a plug flow, or tubular reactor, in which the reactor conditions are typically very different at the inlet and discharge). More than one CSTR may be used.

The reactor also contains a large number of cleaning bodies. The cleaning bodies remain within the reactor during the process of this invention. The reactor is operated on a continuous flow basis—i.e. reactants are added to the reactor and products are removed from the reactor during the operation of the process. Accordingly, it is necessary to design the reactor outlet/product lines to ensure that the cleaning bodies remain within the reactor. A simple screen at the mouth of the product discharge line is one simple design option that may be used to retain the cleaning bodies within the reactor. The use of a hydrocyclone to remove the cleaning bodies from the product stream with centrifugal force is also contemplated.

Specific Process Conditions

The process of the present invention specifically requires a solvent and typically uses a catalyst concentration of from 0.1 to 3×10$^{-6}$ moles of Cr per litre (micromolar).

The reactor temperature is from about 30 to about 130° C., especially from about 35 to about 75° C. and most especially from about 35 to 45° C. In general, lower temperatures have been observed to improve selectivity (when other reaction variables are held constant).

Optimum chromium concentrations have been observed to be from 0.1 to 3 micromolar especially 0.3 to 0.8. Reactor Hold up times (HUT where HUT=reactor volume/flow to reactor) are from 40 to 180 minutes, especially 60 to 90 minutes.

Another preferred element of the present invention is the use of ethylene concentrations of 3 to 15 weight %, especially from 5 to 10 weight %.

The total operating pressure of the process is a function of ethylene concentration, hydrogen concentration, solvent choice and temperature. The use of comparatively low temperature means that a higher ethylene concentration may be achieved at a given pressure (as ethylene solubility increases at lower temperatures). Preferred operating pressures are from 2 to 20 Mega Pascals (MPa) especially from 4 to 10 MPa.

Part E Reactor Control

The control systems required for the operation of agitated reactors are well known to those skilled in the art and do not represent a novel feature of the present invention. In general, temperature, pressure and flow rate readings will provide the basis for most conventional control operations. The increase in process temperature (together with reactor flow rates and the known enthalpy of reaction) may be used to monitor ethylene conversion rates. The amount of catalyst added to the reactor may be increased to increase the ethylene conversion (or conversely, decreased to decrease ethylene conversion) within desired ranges. Thus, basic process control may be derived from simple measurements of temperature, pressure and flow rates using conventional thermocouples, pressure meters and flow meters. Advanced process control (for example, for the purpose of monitoring product selectivity or for the purpose of monitoring process fouling factors) may be undertaken by monitoring additional process parameters with more advanced instrumentation. Known/existing instrumentation that may be employed include in-line/on-line instruments such as NIR infrared, Fourier Transform Infrared (FTIR), Raman, mid-infrared, ultra violet (UV) spectrometry, gas chromatography (GC) analyzer, refractive index, on-line densitometer or viscometer. The use of NIR or GC to measure the composition of the oligomerization reactor and final product composition is especially preferred. A GC analyzer was used to measure the composition of the reactor discharge in the accompanying examples.

The measurement may be used to monitor and control the reaction to achieve the targeted stream properties including but not limited to concentration, viscosity, temperature, pressure, flows, flow ratios, density, chemical composition, phase and phase transition, degree of reaction, polymer content, selectivity.

The control method may include the use of the measurement to calculate a new control set point. The control of the process will include the use of any process control algorithms, which include, but are not limited to the use of PID, neural networks, feedback loop control, forward loop control and adaptive control.

Catalyst Deactivation, Catalyst Removal and Polymer Separation

In general, the oligomerization catalyst is preferably deactivated immediately downstream of the reactor as the product exits the reaction system. This is to prevent polymer formation and potential build up downstream of the reactor and to prevent isomerisation of the 1-olefin product to the undesired internal olefins. It is generally preferred to flash and recover unreacted ethylene before deactivation. However, the option of deactivating the reactor contents prior to flashing and recovering ethylene is also acceptable. The flashing of ethylene is endothermic and may be used as a cooling source.

In general, many polar compounds (such as water, alcohols and carboxylic acids) will deactivate the catalyst. The use of alcohols, amines and/or carboxylic acids is preferred—and combinations of these are contemplated.

The deactivator may be added to the oligomerization product stream before or after the volatile unreacted reagents/diluents and product components are separated. In the event of a runaway reaction (e.g. rapid temperature rise) the deactivator can be immediately fed to the oligomerization reactor to terminate the reaction. The deactivation system may also include a basic compound (such as sodium hydroxide) to minimize isomerization of the products (as activator conditions may facilitate the isomerization of desirable alpha olefins to undesired internal olefins).

The process of this invention causes polymer to flow out of the oligomerization reactor. The polymer exits the reactor with solvent and the oligomer product. This polymer is then separated from the oligomer product.

Polymer separation preferably follows catalyst deactivation. Two "types" of polymer may exist, namely polymer that is dissolved in the process solvent and non-dissolved polymer that is present as a solid or "slurry".

Solid/non-dissolved polymer may be separated using one or more of the following types of equipment: centrifuge; cyclone (or hydrocyclone), a decanter equipped with a skimmer or a filter. Preferred equipment include so called "self-cleaning filters" sold under the name V-auto strainers, self-cleaning screens such as those sold by Johnson Screens Inc. of New Brighton, Minn. and centrifuges such as those sold by Alfa Laval Inc. of Richmond, Va. (including those sold under the trademark Sharples®). The Pall Filter Company also sells filters that are suitable for removing solid polymer from the liquid process stream of this invention.

Soluble polymer may be separated from the final product by two distinct operations. Firstly, low molecular weight polymer that remains soluble in the heaviest product fraction ($C_{20+}$) may be left in that fraction. This fraction will be recovered as "bottoms" from the distillation operations (described below). This solution may be used as a fuel for a power generation system.

An alternative polymer separation comprises polymer precipitation caused by the removal of the solvent from the solution, followed by recovery of the precipitated polymer using a conventional extruder. The technology required for such separation/recovery is well known to those skilled in the art of solution polymerization and is widely disclosed in the literature.

In another embodiment, the residual catalyst is treated with an additive that causes some or all of the catalyst to precipitate. The precipitated catalyst is preferably removed from the product at the same time as by-product polymer is removed (and using the same equipment). Many of the catalyst deactivators listed above will also cause catalyst precipitation. In a preferred embodiment, a solid sorbent (such as clay, silica or alumina) is added to the deactivation operation to facilitate removal of the deactivated catalyst by filtration or centrifugation.

Product Work Up/Distillation

In one embodiment of the present invention, the oligomerization product produced from this invention is added to a product stream from another alpha olefins manufacturing process for separation into different alpha olefins. As previously discussed, "conventional alpha olefin plants" (wherein the term includes i) those processes which produce alpha olefins by a chain growth process using an aluminum alkyl catalyst; ii) the aforementioned "SHOP" process; and iii) the production of olefins from synthesis gas using the so called Lurgi process) have a series of distillation columns to separate the "crude alpha product" (i.e. a mixture of alpha olefins) into alpha olefins (such as butene-1, hexene-1 and octene-1). The mixed hexene-octene product which is preferably produced in accordance with the present invention is highly suitable for addition/mixing with a crude alpha olefin product from an existing alpha olefin plant (or a "cut" or fraction of the product from such a plant) because the mixed hexene-octene product produced in accordance with the present invention can have very low levels of internal olefins. Thus, the hexene-octene product of the present invention can be readily separated in the existing distillation columns of alpha olefin plants (without causing the large burden on the operation of these distillation columns which would otherwise exist if the present hexene-octene product stream contained large quantities of internal olefins). As used herein, the term "liquid product" is meant to refer to the oligomers produced by the process of the present invention which have from 4 to (about) 20 carbon atoms.

In another embodiment, the distillation operation for the oligomerization product is integrated with the distillation system of a solution polymerization plant (as disclosed in Canadian Patent Application No. 2,708,011, Krzywicki et al.).

It will be appreciated that the process solvent must also be separated from the liquid product. This may be done, for example, using distillation. It is highly preferred to recycle the separated solvent back to the oligomerization reactor after it has been distilled/purified.

EXAMPLES

Continuous Operation—General Conditions

A continuously stirred tank reactor (CSTR) having a nominal volume of two liters was used for these experiments.

The CSTR was fitted with external jacket for heating/cooling.

The chromium source for the catalyst was chromium tri(acetylacetonate), or $Cr(acac)_3$. The ligand was a P—N—P ligand in which the nitrogen bridging atom was substituted with an isopropyl group and each P atom was substituted with two ortho-fluoro phenyl groups. This ligand and its synthesis are known to those skilled in the art. Further details are provided in U.S. Pat. No. 8,252,956 (Gao et al.).

The cocatalyst was a combination of modified MAO (MMAO-3A) and TEAL.

MMAO-3A was purchased as a solution of methylaluminoxine (7 weight % Al in isopentane) from Akzo-Nobel.

TEAL was purchased as a 25 wt % TEAL solution in heptane from Akzo-Nobel. Catalyst, ligand and co-catalyst were added to the reactor (i.e. "in situ" catalyst formation).

The reactor was operated in a continuous manner—i.e. product was removed from the reactor during the reaction and feed (ethylene, hydrogen, solvent and catalyst) was added continuously. Ethylene and hydrogen were added to the solvent outside of the reactor and then directed to the reactor via a common feed line. Cyclohexane was used as the solvent in all examples.

The use of two different types of cleaning bodies is reported in Table 1, namely polyethylene and polypropylene pellets.

Using correlation (1)—as described earlier—it was estimated that an agitator speed of 1000 revolutions per minute would be sufficient to suspend the cleaning bodies used in these examples (which had a particle size of about 3 millimeters and a specific gravity of about 1). By way of further explanation, it should be acknowledged that correlation 1 should be regarded as a tool to calculate an estimated value/starting point for the fluid velocity that is required to suspend the cleaning bodies. The value for the fluid velocity that is calculated from correlation 1 can then be verified/confirmed by simple experimentation.

A series of exploratory investigations on the use of different cleaning bodies was undertaken using a mixed vessel (a proxy for a reactor) having transparent plastic walls. The vessel was equipped with different types of agitators and different types of internal components (baffles and draft tubes). These results from the investigations are consistent with the predictions made by the correlations referred to above—in particular, the use of polyethylene (PE) and polypropylene (PP) particles having a density of about 1 gram per cubic centimeter and a particle size of about 3 millimeters was observed to produce a "suspended" mass of cleaning particles at the agitator speeds of the small vessel.

Cleaning bodies were added to the reactor prior to start of each run for each of the invention examples, in the amounts indicated in Table 1.

Cleaning bodies were not used in the comparative examples, which are indicated with a "C" in Table 1—e.g. experiments 1C and 5C. The internal reactor surfaces from these experiments were observed to be completely covered—with the thickness of the polymer coating being quite extreme in some cases.

After each run was completed, the reactor was opened up to remove the cleaning bodies and to determine their effectiveness. The effectiveness of the cleaning bodies was determined by estimating percent of reactor surface area which remained free of polymer deposits. One essential feature of this invention is that foulant is removed from the reactor during operation—i.e. it does not simply accumulate within the reactor and/or on the cleaning bodies. This was confirmed by observing the presence of polyethylene "flakes" in the liquid product that was discharged from the reactor.

The oligomer product that was produced in these examples was typical of that disclosed in U.S. Pat. No. 8,252,956 (Gao et al.) and comprised a combination of hexene and octene oligomers with a minor amount of $C_{10}^+$ oligomers. The amount of reactor fouling in the inventive examples was low—less than 1000 parts per million (by weight) of polymer was deposited on the reactor material surfaces, based on the total amount of ethylene consumed.

TABLE 1

| Run # | Run Length (hr) | Cleaning Body Type | Cleaning Bodies Mass (g) | Reactor [Cr] Concentration (mM) | Al:Cr (mol:mol) | Average Productivity (gProduct/gCr) | Stirring Speed (rpm) | Estimated Percent of Reactor Surface Area Free of Polymer |
|---|---|---|---|---|---|---|---|---|
| [Cr] = 0.67 mM, Al:Cr = 3000, 100 g PP cleaning bodies | | | | | | | | |
| 1C | 18.7 | none | — | 0.66 | 3000 | 4886447 | 1000 | 0 |
| 2 | 9 | PP | 100 | 0.67 | 3000 | 4791209 | 1000 | 95 |
| 3 | 18.3 | PP | 100 | 0.67 | 3000 | 4578755 | 1000 | 55 |

TABLE 1-continued

| Run # | Run Length (hr) | Cleaning Body Type | Cleaning Bodies Mass (g) | Reactor [Cr] Concentration (mM) | Al:Cr (mol:mol) | Average Productivity (gProduct/gCr) | Stirring Speed (rpm) | Estimated Percent of Reactor Surface Area Free of Polymer |
|---|---|---|---|---|---|---|---|---|
| 4 | 22.9 | PP | 100 | 0.67 | 3000 | 4857143 | 850 | 27 |
| 5C | 24.1 | none | — | 0.67 | 3000 | 4688645 | 1000 | 0 |
| [Cr] = 0.34 mM, Al:Cr = 4000, 200 g PP or PE cleaning bodies ||||||||| 
| 6C | 18.2 | none | — | 0.32 | 4000 | 11120879 | 1000 | 0 |
| 7 | 9.3 | PP | 200 | 0.34 | 4000 | 8849817 | 1000 | 75 |
| 8 | 20.5 | PP | 200 | 0.34 | 4000 | 9238095 | 1225 | 65 |
| 9 | 18.7 | PE | 200 | 0.32 | 4000 | 11106227 | 1000 | 30 |
| [Cr] = 1.1-1.2 mM, Al:Cr = 2000 or 3957, 50 or 200 g PE cleaning bodies |||||||||
| 10C | 19.4 | none | — | 1.19 | 2012 | 2620879 | 1000 | 0 |
| 11 | 14.9 | PE | 50 | 1.1 | 2000 | 2410256 | 1000 | 18 |
| 12 | 17.4 | PE | 200 | 1.16 | 3957 | 3343968 | 1000 | 95 |
| [Cr] = 0.33 mM, Al:Cr = 2000, 200 g PP cleaning bodies, stirring Speed = 1000 or 1450 |||||||||
| 13C | 18.2 | none | — | 0.32 | 4000 | 11120879 | 1000 | 0 |
| 14 | 18.2 | PP | 200 | 0.33 | 2000 | 9479853 | 1000 | 25 |
| 15 | 18.9 | PP | 200 | 0.33 | 2000 | 9992674 | 1450 | 55 |

Productivity = grams of oligomer product (hexene + octene) per gram of chromium.

Example 1

Runs 1-5 show the effect of run length on the percent of surface area which remains free of polymer deposits. These runs were done at the same reactor Cr concentration and Al:Cr ratio, both of which have a significant impact on rate of fouling.

Example 2

Runs 6-9 show the similar effect as example 1; however, at lower reactor Cr concentration which shows higher level of fouling even when more cleaning bodies are used.

Example 3

Runs 10-12 show the effect of the mass of cleaning bodies added to the reactor. The reactor was observed to be less fouled as the mass of cleaning bodies is increased.

Example 4

Runs 13-15 show the effect of agitator stirring speed. As the stirring speed is increased from 1000 to 1450 rpm the level of fouling in the reactor was observed to decrease.

Comparative Example

The process of this invention requires that the cleaning particles are suspended in the reaction fluid. As described above, the "just suspended speed" can be calculated/estimated using correlation 1 (and experiments to confirm the calculation may be easily completed).

A comparative experiment was conducted using conditions that were insufficient to provide the just suspended speed. This was done using a dense polymer (a fluoropolymer, designated PFA) and an agitator speed that was too low to suspend the PFA particles. An oligomerization reaction was then completed using oligomerization conditions (temperature, pressure, catalyst and ethylene films, etc.) that were similar to those of experiment 11. At the end of this oligomerization experiment, the reactor was opened and observed to be clean at the bottom of the reactor but heavily fouled elsewhere. This comparative experiment provides further evidence that serves to confirm that:

1) the scouring action of the cleaning bodies is important (this observation is consistent with the observation that flakes of polymer exit the reactor in the liquid product stream. In contrast, if the polymer foulant was simply being deposited upon the cleaning bodies, then the use of suspended cleaning bodies would be less important); and 2) the reactor must be operated at a fluid velocity that is at or above the "just suspended speed" in order to achieve the best results.

It should also be noted that the PFA cleaning bodies would also be suitable for use in the present invention if the agitator speed was sufficient to provide the just suspended speed in the reaction liquid.

INDUSTRIAL APPLICABILITY

The technology of this invention improves the efficiency of an oligomerization process by reducing the rate at which the oligomerization reactor becomes fouled. The oligomers that are prepared by this process may be used as comonomers for the preparation of ethylene copolymers.

The invention claimed is:

1. A process for the removal of by-product polyethylene from a continuous flow, mixed, oligomerization reactor, said process comprising:
   a) providing input flows comprising ethylene, solvent, and an oligomerization catalyst system to said reactor;
   b) oligomerizing ethylene under continuous flow conditions within said reactor; and
   c) providing a discharge stream from said reactor comprising solvent, oligomer product and polyethylene by-product; characterized in that said process is conducted in the presence of a mass of reactor cleaning bodies, with the proviso that substantially all of said cleaning bodies remain within said reactor during said process,
   wherein:
      each of the reactor cleaning bodies has a particle size of from about 2 millimeters to about 2 centimeters, the cleaning bodies have a specific gravity that is greater than a specific gravity of the discharge stream, and the reactor comprises an agitator operated under conditions that are sufficient to suspend at least a portion of the cleaning bodies.

2. The process of claim 1 wherein said reactor is a continuously stirred tank reactor.

3. The process of claim 1 wherein said oligomerization catalyst system comprises a source of active chromium, an activator and a diphosphine ligand defined by the formula $(R^1)(R^2)-P^1\text{-bridge-}P^2(R^3)(R^4)$ wherein $R^1$, $R^2$, $R^3$ and $R^4$ are independently selected from the group consisting of hydrocarbyl and heterohydrocarbyl and said bridge is a moiety that is bonded to both phosphorus atoms.

4. The process of claim 1 wherein said solvent is an aliphatic solvent.

5. The process of claim 1 wherein the total rate of polymer deposition upon the walls of said oligomerization reactor is less than 1000 ppm per hour, based on the total amount of oligomer product.

6. The process of claim 1 wherein said stirred tank reactor is equipped with an agitator that is operated at a speed N (rad/second) greater than the just suspended speed Njs, wherein Njs is calculated by the expression:

$$Njs = S\left(\frac{\mu}{\rho}\right)^{0.1}\left[\frac{g(\rho_p - \rho)}{\rho}\right]^{-0.45} X^{0.13} d_p^{0.2} D^{-0.85} \quad \text{"-Correlation 1-"}$$

where the terms of the correlation are defined as follows (with units in parenthesis):

Njs is the just suspended speed (rad/second),

S a coefficient specific to a particular agitation system (dimensionless),

µ the liquid viscosity (Pascals/seconds),

ρ the liquid density (kilogram/meter$^3$), g the gravitational constant (9.81 meters/second$^2$), ρp the cleaning body density (kilogram/meter$^3$), X the mass ratio of suspended solids to liquid×1000 (dimensionless), dp the cleaning body characteristic diameter (meters), and D the agitator characteristic diameter (meters).

7. The process of claim 1 wherein the cleaning bodies having a density of less than 7 grams per cubic centimeter.

8. The process of claim 1 wherein the cleaning bodies having a density of less than 3 grams per cubic centimeter.

9. The process of claim 1 wherein the cleaning bodies are chosen from polyethylene pellets and polypropylene pellets, and mixtures thereof.

10. The process of claim 1 wherein agitation is accomplished using at least one agitator, at least one draft tube, at least one jet, or combinations thereof.

\* \* \* \* \*